United States Patent [19]

Dusza et al.

[11] 4,178,449
[45] Dec. 11, 1979

[54] PYRAZOLO[1,5-a] PYRIMIDINES AND IMIDAZO-[1,5-a]PYRIMIDINES

[75] Inventors: John P. Dusza; Jay D. Albright, both of Nanuet, N.Y.

[73] Assignee: American Cyanamid Company, Stamford, Conn.

[21] Appl. No.: 970,085

[22] Filed: Dec. 15, 1978

Related U.S. Application Data

[63] Continuation-in-part of Ser. No. 896,826, Apr. 17, 1978.

[51] Int. Cl.² ............... A61K 31/415; C07D 487/04
[52] U.S. Cl. ........................... 544/281; 424/251; 260/570.5 G

[58] Field of Search ........................ 544/281

[56] References Cited

U.S. PATENT DOCUMENTS

| | | |
|---|---|---|
| 3,157,655 | 11/1964 | Takamizawa et al. ............ 544/281 |
| 3,478,029 | 11/1969 | Schicke et al. ................... 544/281 |
| 3,925,385 | 12/1975 | O'Brien et al. ................... 544/281 |

*Primary Examiner*—Donald G. Daus
*Assistant Examiner*—James H. Turnipseed
*Attorney, Agent, or Firm*—Edward A. Conroy, Jr.

[57] ABSTRACT

This disclosure describes substituted pyrazolo[1,5-a]pyrimidines and imidazo[1,5-a]pyrimidines which possess anxiolytic activity.

18 Claims, No Drawings

PYRAZOLO[1,5-a]PYRIMIDINES AND IMIDAZO-[1,5-a]PYRIMIDINES

CROSS REFERENCE TO RELATED APPLICATION

This application is a continuation-in-part of our copending application Ser. No. 896,826, filed Apr. 17, 1978.

BRIEF SUMMARY OF THE INVENTION

This invention relates to new organic compounds and, more particularly, is concerned with novel substituted pyrazolo[1,5-a]pyrimidines (I) and imidazo[1,5-a]pyrimidines (II) which may be represented by the following structural formulae:

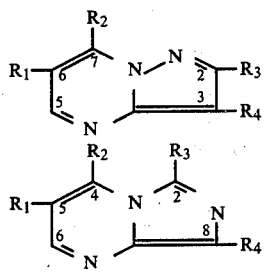

wherein $R_1$ is hydrogen or alkyl having from 1 to 3 carbon atoms; $R_2$ is selected from the group consisting of phenyl, ortho-trifluoromethylphenyl, meta-trifluoromethylphenyl and meta-methoxyphenyl; $R_3$ is hydrogen, fluoro, chloro, bromo, cyano, cyanomethyl, carbamoyl or alkyl having from 1 to 3 carbon atoms; and $R_4$ is selected from the group consisting of hydrogen, fluoro, chloro, bromo, formyl, carboxyl, cyano, hydroxymethyl, N-hydroxyformimidoyl, alkyl having from 1 to 3 carbon atoms and moieties of the formulae:

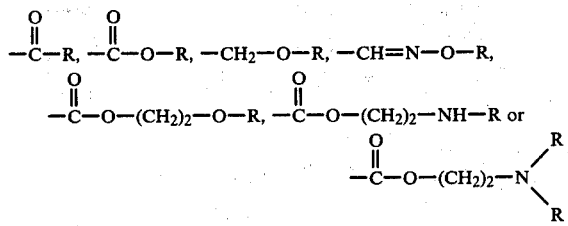

wherein R is alkyl having from 1 to 3 carbon atoms.

DETAILED DESCRIPTION OF THE INVENTION

The novel compounds of the present invention are obtainable as colorless to yellow crystalline materials having characteristic melting points and absorption spectra. They are appreciably soluble in many organic solvents such as lower alkanols, chloroform, tetrahydrofuran, N,N-dimethylformamide and the like but are generally insoluble in water.

The novel 7-(phenyl and substituted phenyl)-pyrazolo-[1,5-a]pyrimidines and 4-(phenyl and substituted phenyl)-imidazo[1,5-a]pyrimidines of the present invention may be readily prepared as set forth in the following reaction scheme:

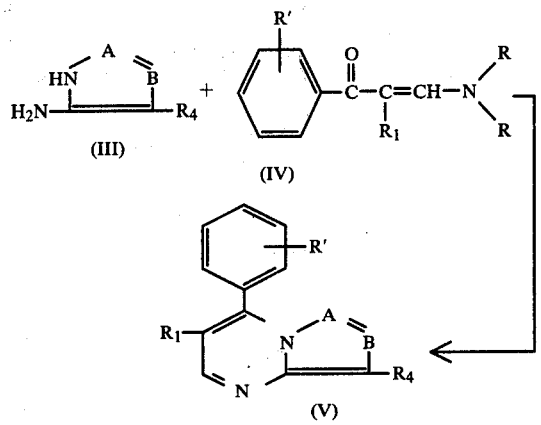

wherein—A=B—is

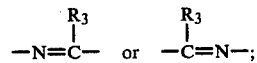

$R'$ is hydrogen, o-trifluoromethyl, m-trifluoromethyl or m-methoxy; and R, $R_1$, $R_3$ and $R_4$ are as hereinabove defined. The reaction of an appropriately substituted 3-aminopyrazole (III where—A=B—is—N=CR$_3$—) or 4-aminoimidazole (III) where—A=B—is—CR$_3$=N—) with an appropriately substituted 3-dialkylaminoacrylophenone (IV) is best carried out in inert organic solvents such as lower alkanols, dioxane, tetrahydrofuran, toluene and the like at the reflux temperature thereof, and with or without acid catalysis. However, the preferred procedure involves the reaction of (III) with (IV) in refluxing glacial acetic acid for a period of 2–24 hours to provide the product (V). The intermediate 3-dialkylaminoacrylophenones (IV) are readily prepared by the reaction of acetophenone, a substituted acetophenone, propiophenone, a substituted propiophenone, butyrophenone or a substituted butyrophenone and the like with a dialkylformamide acetal such as dimethylformamide dimethylacetal at 90°–150° C. for 8–24 hours. The 3-unsubstituted-pyrazolo[1,5-a]pyrimidines (V where—A =B—is—N=CR$_3$—and $R_4$ is hydrogen) may be readily halogenated with reagents such as chlorine, N-chlorosuccinimide, N-chlorobenzotriazole, bromine, N-bromosuccinimide and the like to provide the 3-halo derivatives.

The novel 7-(phenyl and substituted phenyl)-pyrazolo-[1,5-a]pyrimidines and 4-(phenyl and substituted phenyl)-imidazo[1,5-a]pyrimidines of the present invention may also be readily prepared as set forth in the following reaction scheme:

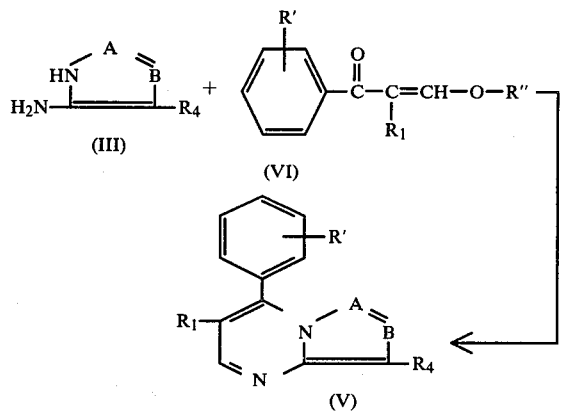

wherein—A=B—, R', R₁, R₃ and R₄ are as hereinbefore defined and R" is hydrogen, alkyl having from 1 to 3 carbon atoms, acetyl, benzoyl or an alkali metal (e.g., sodium, potassium or lithium). The reaction of an appropriately substituted 3-aminopyrazole (III where—A=B—is—N=CR₃—) or 4-aminoimidazole (III where—A=B—is—CR₃=N—) with an appropriate 3-substituted-acrylophenone (VI) is best carried out in inert organic solvents such as lower alkanols, dioxane, tetrahydrofuran, toluene and the like at the reflux temperature thereof and with or without acid catalysis. The reaction is preferably carried out in refluxing glacial acetic acid for a period of 2-24 hours. When R" is an alkali metal such as sodium or potassium, one equivalent of acid is added to give a compound of formula (VI) wherein R" is hydrogen, as an intermediate in the ring closure to compounds of formula (V). Intermediates of formula (VI) where R" is hydrogen, sodium, potassium or lithium may be prepared by formylation of acetophenone, propiophenone, butyrophenone or their substituted forms, and the like, with lower alkyl formates in the presence of alkaline metal alkoxides. Reaction of compounds of formula (VI) where R" is sodium, potassium or lithium with acetic anhydride gives compounds of formula (VI) where R" is acetyl. The reaction of compounds of formula (VI) where R" is hydrogen, sodium, potassium or lithium with anhydrous acids such as hydrochloric acid and the like in the presence of lower alkanols gives the compounds of formula (VI) where R" is alkyl.

The novel compounds of the present invention possess central nervous system activity at non-toxic doses and as such are useful as anxiolytic agents. That is, they produce certain responses in standard tests with laboratory animals which are known to correlate well with relief of anxiety in man. The compounds have been tested pharmacologically and found to have such properties with a desirable wide spread between doses producing anxiolytic activity and toxic symptoms.

The anti-anxiety properties of the novel compounds of the present invention have been established in a test which indicates anxiolytic activity by the measure of protection from convulsions resulting from the administration of pentylenetetrazole. Single or graded dose levels of the test compounds were administered orally or intraperitoneally in a 2% starch vehicle, to groups of at least 4 rats. At 30 or 60 minutes, the rats were treated intravenously with pentylenetetrazole at a dose of 21 to 23 mg./kg. of body weight. This dose is estimated to cause clonic seizures in 99% of unprotected rats. The test compounds are considered active if they protect 50% or more of the rats from clonic seizures. The results of this test with representative compounds of this invention appear in Table I below. It has been reported [R. T. Hill and D. H. Tedeschi, "Animal Testing and Screening Procedures in Evaluating Psychotropic Drugs" in "An Introduction to Psychopharmacology", Eds. R. R. Rech and K. E. Moore, Raven Press, New York, pp. 237–288 (1971)] that there is a high degree of correlation between antagonism of pentylenetetrazole seizures in rats and anti-anxiety effects in higher warm-blooded animals.

Table I

| Compound | Result |
| --- | --- |
| 7-($\alpha,\alpha,\alpha$-Trifluoro-m-tolyl)-pyrazolo-[1,5-a]pyrimidine-3-carbonitrile | Active |
| 2-Methyl-7-($\alpha,\alpha,\alpha$-trifluoro-m-tolyl-pyrazolo[1,5-a]pyrimidine-3-carbonitrile | Active |
| 7-($\alpha,\alpha,\alpha$-trifluoro-m-tolyl)-pyrazolo-[1,5-a]pyrimidine | Active |
| 3-Chloro-7-($\alpha,\alpha,\alpha$-trifluoro-m-tolyl)-pyrazolo[1,5-a]pyrimidine | Active |
| 3-Bromo-7-($\alpha,\alpha,\alpha$-trifluoro-m-toly)-pyrazolo[1,5-a]pyrimidine | Active |
| 7-($\alpha,\alpha,\alpha$-trifluoro-m-tolyl)-pyrazolo-[1,5-a]pyrimidine-3-carboxylic acid ethyl ester | Active |
| 3-Cyano-7-($\alpha,\alpha,\alpha$-trifluoro-m-tolyl)-pyrazolo[1,5-a]pyrimidine-2-carboxamide | Active |
| 6-Methyl-7-($\alpha,\alpha,\alpha$-trifluoro-m-tolyl)-pyrazolo[1,5-a]pyrimidine-3-carbonitrile | Active |
| 7-(m-Methoxyphenyl)pyrazolo[1,5-a]pyrimidine-3-carbonitrile | Active |
| 4-($\alpha,\alpha,\alpha$-Trifluoro-m-tolyl)imidazo[1,5-a]-pyrimidine-8-carbonitrile | Active |
| 5-Phenylpyrazolo[1,5-a]pyrimidine | Active |
| 7-($\alpha,\alpha,\alpha$-Trifluoro-m-tolyl)pyrazolo[1,5-a]-pyrimidine-3-carboxaldehyde, oxime | Active |
| 7-($\alpha,\alpha,\alpha$-trifluoro-m-tolyl)pyrazolo-[1,5-a]-pyrimidine-3-carboxaldehyde | Active |
| 7-($\alpha,\alpha,\alpha$-Trifluoro-m-tolyl)pyrazolo[1,5-a]-pyrimidinyl methyl ketone | Active |
| 3-(Methoxymethyl)-7-($\alpha,\alpha,\alpha$-trifluoro-m-tolyl)pyrazolo[1,5-a]pyrimidine | Active |
| 2-Dimethylaminoethyl 7-($\alpha,\alpha,\alpha$-trifluoro-m-tolyl)pyrazolo[1,5-a]pyrimidine-3-carboxylate | Active |
| Ethyl 4-($\alpha,\alpha,\alpha$-trifluoro-m-tolyl)imidazo-[1,5-a]pyridimine-8-carboxylate | Active |
| 5-($\alpha,\alpha,\alpha$-Trifluoro-m-tolyl)pyrazolo[1,5-a]-pyrimidine | Active |
| Ethyl 7-(m-tolyl)pyrazolo[1,5-a]pyrimidine-3-carboxylate | Active |
| Ethyl 7-(3,4-xylyl)pyrazolo[1,5-a]pyrimidine-3-carboxylate | Active |
| Ethyl 7-(p-ethylphenyl)pyrazolo[1,5-a]pyrimidine-3-carboxylate | Active |
| Ethyl 7-(3,4-dimethoxyphenyl)pyrazolo[1,5-a]-pyrimidine-3-carboxylate | Active |
| 7-(m-Fluorophenyl)pyrazolo[1,5-a]pyrimidine-3-carbonitrile | Active |
| 5-(Phenyl)pyrazolo[1,5-a]pyrimidine | Active |
| 5-($\alpha,\alpha,\alpha$-Trifluoro-m-tolyl)pyrazolo[1,5-a]-pyrimidine | Active |

Another test which has been used to assess anti-anxiety effect is a non-conditioned passive avoidance procedure described by J. R. Vogel, B. Beer and D. E. Clody, "A Simple and Reliable Conflict Procedure for Testing Anti-Anxiety Agents", Psychopharmacologia, 21, 1–7 (1971). A conflict situation is induced in rats by a modification of this method. Groups of 6 naive, Wistar strain rats, weighing 200–240 g. each were deprived of water for 48 hours and food for 24 hours. The test compounds were administered in single or graded, oral or intraperitoneal doses suspended in a 2% starch vehicle containing 0.5% v/v polyethylene glycol and one drop of Polysorbate 80. Control animals received the vehicle alone. At 30 or 60 minutes each rat was placed in individual black plexiglass chambers. A 10% dextrose solution was available ad libitum from a tap located in the rear of the chamber. A 0.3 milliampere constant current 60 Hz pulsed DC shocking current was established between the stainless steel grid floor and the tap. After 20 seconds of non-shocked drinking, an alternating 5 second "shock-on" and 5 second "shock-off" cycle began and continued for a total of 5 minutes. The number of shocks taken by each rat during the 5 minute interval was recorded and compared to a control group. The test compounds are considered active if the shocks received by the test group are significantly different from the control group by the Mann-Whitney U test. The results of this test with representative compounds of this invention appear in Table II below.

Table II

| Compound | Result |
| --- | --- |
| 7-Phenylpyrazolo[1,5-a]pyrimidine | Active |
| 7-($\alpha,\alpha,\alpha$-Trifluoro-m-tolyl)-pyrizolo-[1,5-a]pyrimidine-3-carbonitrile | Active |
| 2-Methyl-7-($\alpha,\alpha,\alpha$-trifluoro-m-tolyl)-pyrazolo[1,5-a]pyrimidine-3-carbonitrile | Active |
| 7-($\alpha,\alpha,\alpha$-Trifluoro-m-tolyl)-pyrazolo-[1,5-a]pyrimidine-3-caboxylic acid ethyl ester | Active |
| 7-($\alpha,\alpha,\alpha$-trifluoro-o-tolyl)-prrazolo-[1,5-a]pyrimidine-3-carbonitrile | Active |
| 6-Methyl-7-($\alpha,\alpha,\alpha$-triflluoro-m-tolyl)-pyrazolo[1,5-a]pyrimidine | Active |
| 3-Chloro-6-methyl-7-($\alpha,\alpha,\alpha$-trifluoro-m-tolyl)pyrazolo[1,5-a]pyrimidine | Active |
| 4-($\alpha,\alpha,\alpha$-trifluoro-m-tolyl)imidazo-[1,5-a]pyrimidine-8-carbonitrile | Active |

Another test used to measure anxiolytic activity comprises measurement of the ability of test compounds to inhibit the binding of $^3$H-diazepam to the brain receptors of warm-blooded animals. The test is described by R. F. Squires in Nature, 266, No. 21 page 732 (April 1977) and H. Mohler and T. Okada, Science, 198, 849 (1977). A modification of this test was employed wherein the animals used were male albino rats of the Wistar strain, weighing 150-200 g. each from Royalhart Farms. Diazepam (methyl-$^3$H) was obtained from New England Nuclear. The test compounds were solubilized in either dimethylformamide, acetic acid, ethanol or hydrochloric acid. Frontal cortex of rats was homogenized gently in 20 volumes of ice-cold 0.32 M. sucrose, centrifuged twice at 1000 g. for 10 minutes and then recentrifuged at 30,000 g. for 20 minutes to produce a crude $P_2$-synaptosomal fraction. The $P_2$-fraction was resuspended, twice the original volume, in hypotonic 50 mM. Tris.HCl (pH 7.4). The binding assay consisted of 300 $\mu$l. of the $P_2$-fraction suspension (0.350 mg.), 100 $\mu$l. of test drug and 100 $\mu$l. of $^3$H-diazepam (1.5 mM.), which was added to 1.5 ml. of 50 mM. Tris.HCl (pH 7.4). Non-specific binding controls and total binding controls received 100 $\mu$l. of diazepam (3 $\mu$m.) and 100 $\mu$l. of deionized water, respectively, in place of the test compound. Incubation for 20 minutes proceeded in ice and was terminated by filtration, under vacuum, through Whatman GF/C glass fiber filters. The filters were washed twice with 5 ml. of ice-cold 50 mM. Tris.HCl (pH 7.4) and placed in scintillation vials. After drying at 50°-60° C. for 30 minutes, 10 ml. of Beckman Ready-Solve HP was added and the radioactivity determined in a Beckman Scintillation Counter. The percentage of inhibition of diazepam binding is calculated for each compound. A compound which exhibits the ability to inhibit binding by $\geq 20\%$ is considered to be active. Representative compounds of the present invention which were active when tested by the diazepam binding assay are set forth in Table III below.

Table III

| Compound | Result |
| --- | --- |
| 7-($\alpha,\alpha,\alpha$-Trifluoro-m-tolyl)-pyrazolo-[1,5-a]pyrimidine-3-carbonitrile | Active |
| 2-Methyl-7-($\alpha,\alpha,\alpha$-trifluoro-m-tolyl)-pyrazolo-[1,5-a]pyrimidine-3-carbonitrile | Active |
| 7-($\alpha,\alpha,\alpha$-Trifluoro-m-tolyl)-pyrazolo-[1,5-a]pyrimidine | Active |
| 3-Chloro-7-($\alpha,\alpha,\alpha$-trifluoro-m-tolyl)-pyrazolo-[1,5-a]pyrimidine | Active |
| 3-Bromo-7-($\alpha,\alpha,\alpha$-trifluoro-m-tolyl)-pyrazolo-[1,5-a]pyrimidine | Active |
| 7-($\alpha,\alpha,\alpha$-Trifluoro-m-tolyl)-pyrazolo-[1,5-a]pyrimidine-3-carboxylic acid ethyl ester | Active |
| 3-Cyano-7-($\alpha,\alpha,\alpha$-trifluoro-m-tolyl)-pyrazolo-[1,5-a]pyrimidine-2-carboxamide | Active |
| 6-Methyl-7-($\alpha,\alpha,\alpha$-trifluoro-m-tolyl)-pyrazolo[1,5-a]pyrimidine-3-carbonitrile | Active |
| 7-(m-Methoxyphenyl)pyrazolo[1,5-a]pyrimidine-3-carbonitrile | Active |
| 4-($\alpha,\alpha,\alpha$-Trifluoro-m-tolyl)imidazo[1,5-a]-pyrimidine-8-carbonitrile | Active |
| 7-Phenylpyrazolo[1,5-a]pyrimidine | Active |
| 7-($\alpha,\alpha,\alpha$-Trifluoro-o-tolyl)-pyrazolo-[1,5-a]pyrimidine-3-carbonitrile | Active |
| 6-Methyl-7-($\alpha,\alpha,\alpha$-trifluoro-m-tolyl)-pyrazolo[1,5-a]pyrimidine | Active |
| 3-Chloro-6-methyl-7-($\alpha,\alpha,\alpha$-trifluoro-m-tolyl)pyrazolo-[1,5-a]pyrimidine | Active |

The novel compounds of the present invention have been found to be highly useful for meliorating anxiety in mammals when administered in amounts ranging from about 0.03 mg. to about 10.0 mg./kg. of body weight per day. A preferred dosage regimen for optimum results would be from about 0.1 mg. to about 5.0 mg./kg. of body weight per day. Such dosage units are employed that a total of from about 7.0 mg. to about 350 mg. of active compound for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compounds may be administered in any convenient manner such as by the oral, intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 0.1 and 5.0 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

This invention will be described in greater detail in conjunction with the following specific examples. The following examples are given for the purpose of illustration and are not intended to limit the scope of the invention.

EXAMPLE 1

7-Phenylpyrazolo[1,5-a]pyrimidine

A reaction mixture of 5.25 g. of 3-dimethylaminoacrylophenone [von H. Meerwein et al., Annalen der Chemie, Band 641, 1-39, (1961)] and 2.50 g. of 3-aminopyrazole in 25 ml. of glacial acetic acid is refluxed for 3.5 hours, cooled overnight and evaporated to a thick yellow oil. This oil is dissolved in methylene chloride, washed with a saturated aqueous solution of sodium bicarbonate, dried over sodium sulfate and then passed through a sintered glass funnel or a chromatographic column packed in vacuo with hydrous magnesium silicate. Additional methylene chloride is passed through the funnel (column). The effluent is refluxed on a steam bath. The gradual addition of hexane produces crystals. The crystallization from methylene chloride with hexane is repeated giving the desired product, m.p. 72°-73° C.

EXAMPLE 2

3-Dimethylamino-3'-(trifluoromethyl)acrylophenone

A reaction mixture of 50 g. of m-trifluoromethylacetophenone and 50 ml. of dimethylformamide dimethylacetal is refluxed for 16 hours under anhydrous conditions and then evaporated in vacuo to a thick orange-red oil. Hexane is added, the mixture is chilled and the desired product is collected by filtration as yellow crystals, m.p. 60.5°-62° C.

EXAMPLE 3

7-(α,α,α-Trifluoro-m-tolyl)pyrazolo[1,5-a]pyrimidine-3-carbonitrile

A mixture of 3.15 g. of 3-dimethylamino-3'-(trifluoromethyl)acrylophenone and 1.40 g. of 3-aminopyrazole-4-carbonitrile in 25 ml. of glacial acetic acid is refluxed for 6 hours. The mixture is evaporated and the residue is treated as described in Example 1, giving the desired product, m.p. 144°-145° C.

EXAMPLE 4

3-Hydroxy-3'-(trifluoromethyl)acrylophenone sodium salt

A mixture of 100 ml. of diethyl ether, 3.36 g. of sodium hydride (60% in oil), 7.4 g. of ethyl formate and 18.8 g. of m-trifluoromethylacetophenone is refluxed with vigorous stirring for 2 hours. The mixture is cooled and the precipitate is recovered by filtration giving 14.6 g. of the desired product, m.p. 200°-201° C.

EXAMPLE 5

3-Hydroxy-3'-(trifluoromethyl)acrylophenone acetate

A suspension of 12.0 g. of 3-hydroxy-3'-(trifluoromethyl)acrylophenone sodium salt in 75 ml. of dioxane and 10 ml. of acetic anhydride is stirred at room temperature for 2 hours and then poured into water. The precipitate is collected by filtration, dissolved in methylene chloride and then passed through a hydrous magnesium silicate column as described in Example 1, giving the desired product, m.p. 55°-57° C.

EXAMPLE 6

7-(α,α,α-Trifluoro-m-tolyl)pyrazolo[1,5-a]pyrimidine-3-carbonitrile

A solution of 0.54 g. of 3-aminopyrazole-4-carbonitrile and 1.29 g. of 3-hydroxy-3'-(trifluoromethyl)acrylophenone acetate in 25 ml. of absolute ethanol is refluxed for 15 hours. The mixture is cooled and filtered giving a solid which is dissolved in methylene chloride and treated as described in Example 1, giving the desired product, m.p. 141°-142.5° C.

EXAMPLE 7

7-Phenylpyrazolo[1,5-a]pyrimidine-3-carbonitrile

A reaction mixture comprising 4.32 g. of 3-aminopyrazole-4-carbonitrile, 7.0 g. of 3-dimethylaminoacrylophenone and 25 ml. of glacial acetic acid is refluxed for 7 hours. The mixture is evaporated and the residue is treated as described in Example 1, giving the desired product, m.p. 230°–232° C.

EXAMPLE 8

7-Phenylpyrazolo[1,5-a]pyrimidine-3-carboxylic acid ethyl ester

A mixture of 17.5 g. of 3-dimethylaminoacrylophenone and 15.52 g. of 3-amino-4-carbethoxypyrazole in 50 ml. of glacial acetic acid is refluxed for 4 hours and then evaporated. The residue is treated as described in Example 1, giving the desired product, m.p. 129°–130° C.

EXAMPLE 9

3-Amino-5-ethylpyrazole-4-carbonitrile

To a solution of 60 g. of ethylethoxymethylene malonitrile in 400 ml. of absolute ethanol is added 22 g. of hydrazine hydrate. The exothermic mixture gives a clear solution. After standing, the solution is concentrated to a gum. Trituration with ether gives the desired product, m.p. 97°–99° C.

EXAMPLE 10

2-Ethyl-7-phenylpyrazolo[1,5-a]pyrimidine-3-carbonitrile

A mixture of 0.71 g. of 3-dimethylaminoacrylophenone, 15 ml. of glacial acetic acid and 0.55 g. of 3-amino-5-ethylpyrazole-4-carbonitrile is refluxed for 16 hours and then evaporated. The residue is treated as described in Example 1, giving the desired product, m.p. 132°–134° C.

EXAMPLE 11

2-Methyl-7-($\alpha,\alpha,\alpha$-trifluoro-m-tolyl)pyrazolo[1,5-a]pyrimidine-3-carbonitrile A mixture of 24.3 g. of 3-dimethylamino-3'-(trifluoromethyl)acrylophenone, 150 ml. of glacial acetic acid and 12.2 g. of 3-methyl-5-aminopyrazole-4-carbonitrile is refluxed for 6 hours and then evaporated. The residue is treated as described in Example 1, giving the desired product, m.p. 149°–150° C.

EXAMPLE 12

7-($\alpha,\alpha,\alpha$-Trifluoro-m-tolyl)pyrazolo[1,5-a]pyrimidine

A mixture of 8.31 g. of 3-aminopyrazole, 24.32 g. of 3-dimethylamino-3'-(trifluoromethyl)acrylophenone and 100 ml. of glacial acetic acid is refluxed for 8 hours and evaporated in vacuo to an oil. This oil is treated as described in Example 1, giving the desired product, m.p. 103°–104.5° C.

EXAMPLE 13

7-($\alpha,\alpha,\alpha$-Trifluoro-m-tolyl)pyrazolo[1,5-a]pyrimidine

A mixture of 0.83 g. of 3-aminopyrazole and 2.38 g. of 3-hydroxy-3'-(trifluoromethyl)acrylophenone sodium salt in 25 ml. of glacial acetic acid is refluxed for 15 hours and then concentrated to dryness. The residue is treated as described in Example 1, giving the desired product, m.p. 104°–106° C.

EXAMPLE 14

3-Chloro-7-($\alpha,\alpha,\alpha$-trifluoro-m-tolyl)pyrazolo[1,5-a]pyrimidine A 3.3 g. portion of N-chlorobenzotriazole is added to a solution of 5.26 g. of 7-($\alpha,\alpha,\alpha$-trifluoro-m-tolyl)-pyrazolo[1,5-a]pyrimidine in 50 ml. of chloroform producing an exothermic reaction. The mixture is refluxed on a steam bath for 15 minutes, cooled to room temperature and then poured into an ice-cold solution of 2.5 N sodium hydroxide. The organic layer is separated, dried over sodium sulfate and passed through a hydrous magnesium silicate column. The effluent is heated to reflux and hexane is added giving a solid. The solid is dissolved in methylene chloride re-processed through the column and precipitated from refluxing solution with hexane giving crystals of the desired product, m.p. 155°–157° C.

EXAMPLE 15

3-Bromo-7-($\alpha,\alpha,\alpha$-trifluoro-m-tolyl)pyrazolo[1,5-a]pyrimidine A 3.75 g. portion of N-bromosuccinimide is added to a solution of 5.26 g. of 7-($\alpha,\alpha,\alpha$-trifluoro-m-tolyl)-pyrazolo[1,5-a]pyrimidine in 50 ml. of chloroform producing an exothermic reaction. The mixture is refluxed on a steam bath for 15 minutes and then treated as described in Example 14, giving the desired product, m.p. 138°–140° C.

EXAMPLE 16

7-($\alpha,\alpha,\alpha$-Trifluoro-m-tolyl)pyrazolo[1,5-a]pyrimidine-3-carboxylic acid ethyl ester A mixture of 5.0 g. of 3-amino-4-carbethoxypyrazole and 7.84 g. of 3-dimethylamino-3'-(trifluoromethyl)acrylophenone in 25 ml. of glacial acetic acid is refluxed for 6 hours and then evaporated in vacuo to an oil. This oil is treated as described in Example 1, giving the desired product, m.p. 97°–99° C.

EXAMPLE 17

7-($\alpha,\alpha,\alpha$-Trifluoro-m-tolyl)pyrazolo[1,5-a]pyrimidine-3-carboxylic acid sodium salt A mixture of 3.35 g. of 7-($\alpha,\alpha,\alpha$-trifluoro-m-tolyl)-pyrazolo[1,5-a]pyrimidine-3-carboxylic acid ethyl ester, 20 ml. of 5 N sodium hydroxide and 75 ml. of ethanol is heated on a steam bath for 4 hours. The mixture is cooled and solid is recovered by filtration giving the desired product, m.p. 322°–325° C. (dec.).

Substitution of potassium hydroxide in the above reaction gives the potassium salt of the title compound, m.p. 375°–380° C. (dec.).

EXAMPLE 18

7-($\alpha,\alpha,\alpha$-Trifluoro-m-tolyl)pyrazolo[1,5-a]pyrimidine-3-carboxylic acid A mixture of 0.70 g. of 7-($\alpha,\alpha,\alpha$-trifluoro-m-tolyl)-pyrazolo[1,5-a]pyrimidine-3-carboxylic acid sodium salt, 25 ml. of methylene chloride and 10 ml. of 1 N hydrochloric acid is stirred overnight. The solid which forms is collected by filtration. The filtrate is evaporated to produce more solid. The solids are combined and recrystallized from methylene chloride giving the desired product, m.p. 248°–250° C.

EXAMPLE 19

3-Cyano-7-(α,α,α-trifluoro-m-tolyl)pyrazolo[1,5-a]pyrimidine-2-carboxamide

A mixture of 4.86 g. of 3-dimethylamino-3'-(trifluoromethyl)acrylophenone, 50 ml. of glacial acetic acid and 2.66 g. of 3-aminopyrazole-4,5-dicarbonitrile is refluxed for 16 hours and then evaporated. The residue is treated as described in Example 1, giving the desired product, m.p. 236°–238° C.

EXAMPLE 20

3-Dimethylamino-2'-(trifluoromethyl)acrylophenone

A mixture of 35 g. of o-trifluoromethylacetophenone in 35 ml. of dimethylformamide dimethylacetal is refluxed for 8 hours under anhydrous conditions and then evaporated to a yellow oil. Bulb to bulb distillation gives the desired product as a thick yellow oil.

EXAMPLE 21

7-(α,α,α-Trifluoro-o-tolyl)pyrazolo[1,5-a]pyrimidine-3-carbonitrile

A mixture of 4.86 g. of 3-dimethylamino-2'-(trifluoromethyl)acrylophenone, 50 ml. of glacial acetic acid and 3.24 g. of 3-aminopyrazole-4-carbonitrile is refluxed for 9 hours and evaporated to a residue. The residue is treated as described in Example 1, giving the desired product, m.p. 195.5°–197° C.

EXAMPLE 22

3-Dimethylamino-2-methyl-3'-(trifluoromethyl)acrylophenone

A mixture of 25 g. of m-trifluoromethylpropiophenone and 25 ml. of dimethylformamide dimethylacetal is refluxed overnight and then evaporated to an oil. The oil is dissolved in hexane and the solution is refrigerated giving crystals of the desired product, m.p. 53°–55° C.

The perchlorate salt may be prepared by treatment of the above product with triethylorthoformate, perchloric acid and ether, m.p. 142°–145° C.

EXAMPLE 23

6-Methyl-7-(α,α,α-trifluoro-m-tolyl)pyrazolo-[1,5-a]pyrimidine-3-carbonitrile

A mixture of 1.08 g. of 3-aminopyrazole-4-carbonitrile, 25 ml. of glacial acetic acid and 2.57 g. of 3-dimethylamino-2-methyl-3'-(trifluoromethyl)acrylophenone is refluxed for 8 hours and then evaporated to a crystalline solid. A methylene chloride solution of this solid is treated as described in Example 1, giving the desired product, m.p. 191°–193° C.

EXAMPLE 24

6-Methyl-7-(α,α,α-trifluoro-m-tolyl)pyrazolo[1,5-a]pyrimidine

A mixture of 1.84 g, of 3-aminopyrazole, 50 ml. of glacial acetic acid, 1.80 g. of sodium acetate and 7.90 g. of 3-dimethylamino-2-methyl-3'-(trifluoromethyl)acrylophenone perchlorate is refluxed for 6 hours and then evaporated. The residue is reacted as described in Example 1, giving the desired product, m.p. 168°–169° C.

EXAMPLE 25

3-Chloro-6-methyl-7-(α,α,α-trifluoro-m-tolyl)-pyrazolo[1,5-a]pyrimidine

A mixture of 2.77 g. of 6-methyl-7-(α,α,α-trifluoro-m-tolyl)pyrazolo[1,5-a]pyrimidine, 100 ml. of chloroform and 1.68 g. of N-chlorobenzotriazole is refluxed for 20 minutes, allowed to stand at room temperature for 30 minutes and then poured into 1 N sodium hydroxide in an ice bath. The product is separated, dried over sodium sulfate and treated as described in Example 1, giving the desired product, m.p. 195°–197° C.

EXAMPLE 26

3-Dimethylamino-3'-methoxyacrylophenone

A mixture of 25 g. of m-methoxyacrylophenone and 25 ml. of dimethylformamide dimethyl acetal is refluxed for 12 hours. Removal of any volatile material in vacuo gives a thick oil. Bulb to bulb distillation gives the desired product.

EXAMPLE 27

7-(m-Methoxyphenyl)pyrazolo[1,5-a]pyrimidine-3-carbonitrile

A mixture of 6.15 g. of 3-dimethylamino-3'-methoxyacrylophenone and 3.16 g. of 3-aminopyrazole-4-carbonitrile in 50 ml. of glacial acetic acid is refluxed for 15 hours and then cooled. The precipitate is recovered by filtration giving the desired product, m.p. 165°–166° C.

EXAMPLE 28

4-(α,α,α-Trifluoro-m-tolyl)imidazo[1,5-a]pyrimidine-8-carboxamide

A mixture of 1.62 g. of 4-amino-5-imidazolecarboxamide hydrochloride, 2.43 g. of 3-dimethylamino-3'-trifluoromethylacrylophenone and 0.82 g. of sodium acetate in 25 ml. of glacial acetic acid is refluxed for 15 hours and then evaporated to dryness. The residue is treated as described in Example 1, giving the desired product, m.p. 239°–240° C.

EXAMPLE 29

4-(α,α,α-Trifluoro-m-tolyl)imidazo[1,5-a]pyrimidine-8-carbonitrile

A mixture of 2.0 g. of 4-(α,α,α-trifluoro-m-tolyl)imidazo[1,5-a]pyrimidine-8-carboxamide, 1.03 g. of anhydrous pyridine and 50 ml. of anhydrous dioxane is chilled in an ice bath. To this is added 1.51 g. of trifluoroacetic anhydride and the mixture is stirred at room temperature overnight. Water is added and the resulting solid is collected by filtration. This solid is dissolved in methylene chloride and passed through a column of hydrous magnesium silicate. The effluent is refluxed with the continued addition of hexane until crystallization is started. Cooling gives the desired solid product which is recovered by filtration, m.p. 168°–169° C.

EXAMPLE 30

2-Ethyl-7-(α,α,α-trifluoro-m-tolyl)pyrazolo[1,5-a]pyrimidine-3-carbonitrile

A mixture of 7.29 g. of 3-dimethylamino-3'-(trifluoromethyl)acrylophenone and 4.08 g. of 3-amino-5-ethylpyrazole-4-carbonitrile in 25 ml. of glacial acetic acid is refluxed for 15 hours and then evaporated to a residue. This residue is treated as described in Example 1, giving the desired product, m.p. 144°–146° C.

EXAMPLE 31

2-Ethyl-6-methyl-7-($\alpha,\alpha,\alpha$-trifluoro-m-tolyl)-pyrazolo[1,5-a]pyrimidine-3-carbonitrile A mixture of 2.52 g. of 3-dimethylamino-2-methyl-3'-(trifluoromethyl)acrylophenone and 1.36 g. of 3-amino-5-ethylpyrazole-4-carbonitrile in 25 ml. of glacial acetic acid is refluxed for 15 hours and then evaporated to a residue. The residue is treated as described in Example 1, giving the desired product, m.p. 163°–164° C.

EXAMPLE 32

4-($\alpha,\alpha,\alpha$-Trifluoro-m-tolyl)imidazo[1,5-a]pyrimidine

A mixture of 2 g. of ethyl 4-($\alpha,\alpha,\alpha$-trifluoro-m-tolyl)imidazo[1,5-a]pyrimidine-8-carboxylate, 2 g. of potassium hydroxide and 50 ml. of ethanol:water (9:1) is refluxed for 4 hours. The mixture is concentrated, diluted with water and the solid 4-($\alpha,\alpha,\alpha$-trifluoro-m-tolyl)imidazo[1,5-a]pyrimidine-8-carboxylic acid isolated. The preceding compound is heated neat at 190° C. to give the product of the example.

EXAMPLE 33

8-Methyl-4-($\alpha,\alpha,\alpha$-trifluoro-m-tolyl)imidazo[1,5-a]pyrimidine

A solution of 0.010 mole of 4-($\alpha,\alpha,\alpha$-trifluoro-m-tolyl)imidazo[1,5-a]pyrimidine-8-carboxylic acid in tetrahydrofuran is added dropwise to a 0.02 molar solution of diborane in tetrahydrofuran chilled in an ice bath. The mixture is allowed to warm to room temperature and stand overnight. The mixture is poured onto ice and extracted with methylene chloride. The methylene chloride extract is washed with water and dried (MgSO$_4$). The solvent is removed under reduced pressure to give the product of the example.

EXAMPLE 34

4-($\alpha,\alpha,\alpha$-Trifluoro-m-tolyl)imidazo[1,5-a]pyrimidine-8-carboxaldehyde A 0.01 mole sample of 4-($\alpha,\alpha,\alpha$-trifluoro-m-tolyl)-imidazo[1,5-a]pyrimidine-8-carbonitrile in tetrahydrofuran at −40° C. is reacted with diisobutyl aluminum hydride. To the mixture is added saturated aqueous ammonium chloride followed by dilute sulfuric acid. The mixture is extracted with methylene chloride and the extract washed with water and dried (MgSO$_4$). The solvent is removed under reduced pressure to give the product of the example.

EXAMPLE 35

8-Chloro-4-($\alpha,\alpha,\alpha$-trifluoro-m-tolyl)imidazo[1,5-a]pyrimidine

To a solution of 0.01 mole of 4-($\alpha,\alpha,\alpha$-trifluoro-m-tolyl)imidazo[1,5a]pyrimidine in chloroform is added 0.011 mole of N-chlorosuccinimide. The mixture is heated on a steam bath for one hour, cooled and poured into an ice-cold solution of 2.5 N sodium hydroxide. The organic layer is separated, dried (MgSO$_4$) and passed through a column of hydrous magnesium silicate with chloroform as eluent. The eluent is concentrated to dryness to give the product of the example.

EXAMPLE 36

3-Methyl-7-($\alpha,\alpha,\alpha$-trifluoro-m-tolyl)pyraziolo[1,5-a]pyrimidine

A mixture of 0.01 mole of 3-amino-4-methylpyrazole and 0.01 mole of 3-dimethylamino-3'-(trifluoromethyl)acrylophenone in glacial acetic acid is refluxed for 6 hours. The solvent is removed and the residue dissolved in methylene chloride and passed through a column of hydrous magnesium silicate. Concentration of the eluent and addition of hexane gives the product of the example.

EXAMPLE 37

3-Methyl-7-($\alpha,\alpha,\alpha$-trifluoro-m-tolyl)pyrazolo[1,5-a]pyrimidine

A solution of 0.01 mole of 7-($\alpha,\alpha,\alpha$-trifluoro-m-tolyl)-pyrazolo[1,5-a]pyrimidine-3-carboxylic acid in tetrahydrofuran is added dropwise to a chilled (0° C.) solution of 0.02 mole of diborane in tetrahydrofuran. After standing overnight the mixture is poured onto ice and the product extracted into dichloromethane. The dichloromethane layer is washed with water, dried (MgSO$_4$) and the solvent removed to give the product of the example.

EXAMPLE 38

4-($\alpha,\alpha,\alpha$-Trifluoro-m-tolyl)imidazo[1,5-a]pyrimidine-8-carbonitrile A mixture of 1.0 g. of 8-bromo-4-($\alpha,\alpha,\alpha$-trifluoro-m-tolyl)imidazo[1,5-a]pyrimidine, 0.45 g. of cuprous cyanide and 25 ml. of N,N-dimethylformamide is refluxed for 16 hours. The solvent is removed under reduced pressure. The residue is extracted with methylene chloride and the solution passed through a column of hydrous magnesium silicate. The eluent is collected, concentrated and n-hexane added while heating. The product separates as crystals, m.p. 168°–169° C.

EXAMPLE 39

4-($\alpha,\alpha,\alpha$-Trifluoro-m-tolyl)-8-bromoimidazo[1,5-a]pyrimidine

A mixture of 0.01 mole of 3-dimethylamino-3'-(trifluoromethyl)acrylophenone, 0.01 mole of 4-amino-5-bromoimidazole and 50 ml. of glacial acetic acid is refluxed for 6 hours. The solvent is removed and the residue worked up as for Example 29 to give the product of the example.

EXAMPLE 40

4-($\alpha,\alpha,\alpha$-Trifluoro-m-tolyl)-8-chloroimidazo[1,5-a]pyrimidine

A mixture of 0.01 mole of 3-dimethylamino-3'-(trifluoromethyl)acrylophenone, 40 ml. of glacial acetic acid and 0.01 mole of 4-amino-5-chloroimidazole is refluxed for 6 hours. The solvent is removed under reduced pressure and the residue worked up as for Example 29 to give the product of the example.

EXAMPLE 41

2-Methyl-4-($\alpha,\alpha,\alpha$-trifluoro-m-tolyl)imidazo[1,5-a]pyrimidine-8-carbonitrile A mixture of 0.01 mole of 3-dimethylamino-3'-(trifluoromethyl)acrylophenone, 50 ml. of glacial acetic acid and 0.01 mole of 4-amino-5-imidazolecarbonitrile is refluxed for 5 hours. The solvent is removed under reduced pressure and the residue worked up as for Example 29 to give the product of the example.

EXAMPLE 42

4-(α,α,α-Trifluoro-m-tolyl)imidazo[1,5-a]pyrimidine-8-methanol

A mixture of ethyl 4-(α,α,α-trifluoro-m-tolyl)imidazo[1,5-a]pyrimidine-8-carboxylate is reduced with lithium aluminum hydride in refluxing tetrahydrofuran to give the product of the example.

EXAMPLE 43

3-Cyano-7-(α,α,α-trifluoro-m-tolyl)pyrazolo-[1,5-a]pyrimidine-2-carbonitrile

A mixture of 4.86 g. of 3-dimethylamino-3'-(trifluoromethyl)acrylophenone, 50 ml. of glacial acetic acid and 2.66 g. of 3-aminopyrazole-4,5-dicarbonitrile is refluxed for 10 hours and the solvent removed under reduced pressure. The residue is treated with trifluoroacetic anhydride to give the product of the example. cl

EXAMPLE 44

4-(α,α,α-Trifluoro-m-tolyl)imidazo[1,5-a]pyrimidine-8-carbonitrile

A mixture of 0.01 mole of 3-dimethylamino-3'-(trifluoromethyl)acrylophenone and 0.01 mole of 4-amino-5-imidazolecarbonitrile in 30 ml. of glacial acetic acid is refluxed for 6 hours. The solvent is removed under reduced pressure and worked up as for Example 29 to give the product as crystals, m.p. 168°–169° C.

EXAMPLE 45

4-(α,α,α-Trifluoro-o-tolyl)imidazo[1,5-a]pyrimidine-8-carbonitrile

A mixture of 1.62 g. of 4-amino-5-imidazolecarboxamide hydrochloride, 0.82 g. of sodium acetate and 25 ml. of glacial acetic acid is refluxed for 10 hours. The mixture is evaporated to dryness and the residue worked up as for Example 1 to give 4-(α,α,α-trifluoro-m-tolyl)imidazo[1,5-a]pyrimidine-8-carboxamide. This compound is treated with trifluoroacetic anhydride as for Example 29 to give the product of the example.

EXAMPLE 46

4-(m-Methoxyphenyl)imidazo[1,5-a]pyrimidine-8-carbonitrile

A mixture of 1.62 g. of 4-amino-5-imidazolecarboxamide hydrochloride, 3-dimethylamino-3'-methoxyacrylophenone, 0.82 g. of sodium acetate and 25 ml. of glacial acetic acid is refluxed for 10 hours. The mixture is evaporated to dryness and the residue worked up to give 4-(m-methoxyphenyl)imidazo[1,5-a]pyrimidine-8-carboxamide. This compound is treated as for Example 29 with trifluoroacetic anhydride to give the product of the example.

EXAMPLE 47

7-(α,α,α-Trifluoro-m-tolyl)pyrazolo[1,5-a]pyrimidine

A sample of 7-(m-cyanophenyl)pyrazolo[1,5-a]pyrimidine is heated with acetic acid-hydrochloric acid to give 7-(m-carboxyphenyl)pyrazolo[1,5-a]pyrimidine. The preceding compound is heated with sulfur tetrafluoride for 20 hours at 150° C. to give the product of the example, m.p. 104°–106° C.

EXAMPLE 48

7-(α,α,α-Trifluoro-m-tolyl)pyrazolo[1,5-a]pyrimidine-3-carboxaldehyde

Five millimeters of phosphorus oxychloride is added dropwise to an ice cooled solution of 25 ml. of dimethylformamide and when this is complete 5.26 g. of 7-(α,α,α-trifluoro-m-tolyl)pyrazolo[1,5-a]pyrimidine is added and the reaction mixture is heated on a steam bath for one hour. This is poured onto ice and made strongly basic to yield the desired compound, recovered by subsequent filtration, m.p. 168°–170° C.

EXAMPLE 49

7-(α,α,α-Trifluoro-m-tolyl)pyrazolo[1,5-a]pyrimidine-3-carboxaldehyde, oxime

A mixture of 2.91 g. of 7-(α,α,α-trifluoro-m-tolyl)pyrazolo[1,5-a]pyrimidine-3-carboxaldehyde, 0.90 g. of anhydrous sodium acetate, 0.50 g. of hydroxylamine hydrochloride and 50 ml. of ethanol was heated on a steam bath for one hour and then water is added to turbidity. On cooling, the oxime precipitates from solution and is recovered by filtration, m.p. 196°–197° C.

EXAMPLE 50

7-(α,α,α-Trifluoro-m-tolyl)pyrazolo[1,5-a]pyrimidine-3-carbonitrile

A solution of 1.0 g. of 7-(α,α,α-trifluoro-m-tolyl)pyrazolo[1,5-a]pyrimidine-3-carboxaldehyde, oxime and 25 ml. acetic anhydride is refluxed for 16 hours. Evaporation of the solvent gives a solid, which when recrystallized from methylene chloride-n-hexane gives the desired nitrile, m.p. 141°–143° C.

EXAMPLE 51

7-(α,α,α-Trifluoro-m-tolyl)pyrazolo[1,5-a]pyrimidine-3-carbonitrile

A mixture of 0.95 g. of 3-bromo-7-(α,α,α-trifluoro-m-tolyl)pyrazolo[1,5-a]pyrimidine, 0.45 g. cuprous cyanide and 25 ml. of dimethylformamide is refluxed for 16 hours. Evaporation of the reaction mixture gave a residue which has triturated with methylene chloride. The methylene chloride solution is passed through a short column of hydrous magnesium silicate. The effluent is collected and refluxed on a steam bath with gradual addition of n-hexane and the desired nitrile crystallized from solution, m.p. 141°–143° C.

EXAMPLE 52

7-(α,α,α-Trifluoro-m-tolyl)pyrazolo[1,5-a]pyrimidine-3-carbonitrile

One gram of 7-(α,α,α-trifluoro-m-tolyl)pyrazolo[1,5-a]pyrimidine-3-carboxamide and 5 ml. of phosphorus oxychloride is refluxed for 3 hours. The reaction mixture is evaporated to dryness and the residue is dissolved in methylene chloride, washed with saturated sodium bicarbonate solution, dried with anhydrous sodium sulfate. After passing through a short pad of hydrous magnesium silicate with eluent methylene chloride. Concentration of the eluent with addition of n-hexane gives the product, m.p. 141°–143° C.

EXAMPLE 53

α-Methyl-7-(α,α,α-trifluoro-m-tolyl)pyrazolo[1,5-a]pyrimidine-3-methanol

An ethereal solution of methyl magnesium iodide is prepared from 0.75 g. magnesium and 4.20 g. methyl iodide in 50 ml. anhydrous diethyl ether. A slurry of 5.82 g. of 7-(α,α,α-trifluoro-m-tolyl)pyrazolo[1,5-a]pyrimidine-3-carboxaldehyde in 100 ml. of anhydrous ether is added and the reaction mixture is refluxed for 2 hours. After cooling, water is added and the mixture acidified with 1N HCl, separated and the organic layer evaporated to give a solid. Recrystallization from methylene chloride-hexane gave the desired alcohol, m.p. 155°–158° C.

EXAMPLE 54

Methyl 7-(α,α,α-trifluoro-m-tolyl)pyrazolo[1,5-a]pyrimid-3-yl ketone

A mixture of 3.0 g. of α-methyl-7-(α,α,α-trifluoro-m-tolyl)pyrazolo[1,5-a]pyrimidine-3-methanol and one gram of chromium trioxide in 75 ml. glacial acetic acid is allowed to remain at room temperature for 1 hour and then poured into water. The resultant solid is removed by filtration and then recrystallized from methylene chloride-n-hexane to yield the desired methyl ketone, m.p. 127°–130° C.

EXAMPLE 55

7-Phenylpyrazolo[1,5-a]pyrimidine-3-methanol

A mixture of 2.23 g. of 7-phenylpyrazolo[1,5-a]pyrimidine-3-carboxaldehyde and 0.37 g. sodium borohydride in 100 ml. of methanol is stirred for 16 hours. The reaction mixture is evaporated to dryness and methylene chloride is added. This solution is washed with a saturated sodium bicarbonate solution and is passed through a hydrous magnesium silicate column. Addition of hexane to the effluent gave the hydroxymethyl compound, m.p. 124°–125° C.

EXAMPLE 56

Ethyl 4-(α,α,α-trifluoro-m-tolyl)imidazolo[1,5-a]pyrimidine-8-carboxylate

A mixture of 1.55 g. of ethyl 5-aminoimidazole-4-carboxylate and 2.43 g. of 3-dimethylamino-3'-trifluoromethylacrylophenone in 25 ml. of glacial acetic acid is refluxed for 6 hours. On cooling the product crystallized from solution, m.p. 232°–234° C.

EXAMPLE 57

Ethyl 4-phenylimidazolo[1,5-a]pyridimine-8-carboxylate

A mixture of 1.55 g. of ethyl 5-aminoimidazole-4-carboxylate and 1.75 g. of 3-dimethylaminoacrylophenone in 25 ml. glacial acetic acid is refluxed for 6 hours and when cooled no precipitate formed. The reaction mixture is evaporated to dryness and dissolved in methylene chloride. After being washed with a saturated sodium bicarbonate solution and dried with anhydrous sodium sulfate, the solution was passed through a short column of hydrous magnesium silicate. Hexane addition to this solution gave the desired product, m.p. 200°–204° C.

EXAMPLE 58

3',4'-Dimethoxy-3-dimethylaminoacrylophenone

A mixture of 50.0 g. of 3',4'-dimethyoxyacetophenone and 50 ml. of dimethylformamide dimethylacetal is refluxed for 16 hours. On cooling the desired compound crystallizes from solution. Hexane is added and the material is recovered by filtration, m.p. 124°–125° C.

EXAMPLE 59

Ethyl 7-(3,4-dimethoxyphenyl)pyrazolo[1,5-a]pyrimidine-3-carboxylate

A mixture of 2.35 g. of 3-dimethylamino-3',4'-dimethyoxyacrylophenone and ethyl 3-aminopyrazole-4-carboxylate in 25 ml. of glacial acetic acid is refluxed for 20 hours and worked up to give the product, m.p. 148°–149° C.

EXAMPLE 60

3-Dimethylamino-4'-ethylacrylophenone

A mixture of 50 g. of 4'-ethylacetophenone and 50 ml. of dimethylformamide dimethylacetal is refluxed for 16 hours. Evaporation gave a thick oil which crystallized on the addition of hexane, m.p. 80°–81° C.

EXAMPLE 61

Ethyl 7-(p-ethylphenyl)pyrazolo[1,5-a]pyrimidine-3-carboxylate

A mixture of 4.07 g. of 3-dimethylamino-4'-ethylacrylophenone and 3.10 g. of ethyl 3-aminopyrazole-4-carboxylate in 25 ml. of glacial acetic acid is refluxed for 20 hours. The compound is recovered from the reaction in the previously described fashion to yield crystals, m.p. 101°–103° C.

EXAMPLE 62

3',4'-Dimethyl-3-dimethylaminoacrylophenone

A mixture of 50 g. of 3',4'-dimethylacetophenone and 50 ml. of dimethylformamide dimethylacetal is refluxed for 16 hours. On cooling the desired compound crystallizes from the reaction mixture. After hexane is added, the desired compound is recovered by filtration, m.p. 108°–110° C.

EXAMPLE 63

Ethyl 7-(3,4-xylyl)pyrazolo[1,5-a]pyrimidine-3-carboxylate

A mixture of 4.06 g. of 3',4'-dimethyl-3-dimethylaminoacrylophenone and 3.10 g. of ethyl 3-aminopyrazole-4-carboxylate in 25 ml. of glacial acetic acid is refluxed for 6 hours. The desired compound is recovered as in previous examples except that the compound as first observed is amorphous and then crystallizes on standing in the crystallization solvent, m.p. 187°–188° C.

EXAMPLE 64

7-Hydroxy-5-(α,α,α-trifluoro-m-tolyl)pyrazolo[1,5-a]pyrimidine

A mixture of 0.83 g. of 3-aminopyrazole and 2.61 g. of ethyl m-trifluoromethylbenzoylacetate is heated on a steam bath for 2 hours. After cooling the desired compound is collected by filtration, m.p. 305°–310° C.

EXAMPLE 65

7-Chloro-5(α,α,α-trifluoro-m-tolyl)pyrazolo[1.5-a]pyrimidine

A mixture of 1.75 g. of 7-hydroxy-5-(α,α,α-trifluoro-m-tolyl) pyrazolo[1,5-a]pyrimidine and 15 ml. of phosphorus oxychloride is refluxed for 2 hours. After evaporation at reduced pressure, ice is added to the residue and the desired compound is extracted with methylene chloride. After washing the organic layer with a saturated saline solution and drying with solid anhydrous sodium sulfate, evaporation gives the desired compound, m.p. 137°–139° C.

EXAMPLE 66

5-(α,α,α-Trifluoro-m-tolyl)pyrazolo[1,5-a]pyrimidine

The mixture of 1.65 g. 7-chloro-5-(α,α,α-trifluoro-m-tolyl) pyrazolo[1,5a]pyrimidine, 0.46 g. of anhydrous sodium acetate, 0.20 g. of 10% palladium on charcoal catalyst and 100 ml. of absolute alcohol is hydrogenated in a Parr apparatus beginning at 10 lbs. pressure until one equivalent of hydrogen is absorbed in about 40 minutes. the catalyst is removed by filtration and the solvent is evaporated to dryness and water is added. The solid is collected by filtration and is recrystallized from methylene chloride-hexane to yield the desired material, m.p. 117°–118° C.

EXAMPLE 67

5-Phenylpyrazolo[1,5-a]pyrimidine

A mixture of 2.29 g. of 5-chloro-7-phenylpyrazolo-[1,5-a]pyrimidine, 0.90 g. anhydrous sodium acetate, and 0.30 g. of 10% palladium on charcoal catalyst in 100 ml. of absolute alcohol is hydrogenated at 10 lbs. pressure. Uptake stops in 45 minutes and catalyst is filtered. Evaporation and solution in methylene chloride with passage through a short hydrous magnesium silicate column gives the solution from which the desired compound crystallizes upon the addition of hexane, m.p. 122°–124° C.

EXAMPLE 68

Ethyl 2-ethyl-7-(α,α,α-trifluoro-m-tolyl)pyrazolo[1,5-a]-pyrimidine-3-carboxylate As for Example 1, ethyl 3-amino-5-ethyl-pyrazole-4-carboxylate is reacted with 3-dimethylamino-3'-(trifluoromethyl) acrylophenone to give the product as crystals, m.p. 142°–143° C.

EXAMPLE 69

Ethyl 2-ethyl-7-phenylpyrazolo[1,5-a]pyrimidine-3-carboxylate

As for example 1, ethyl 3-amino-5-ethyl-pyrazole-3-carboxylate is reacted with 3-dimethylamino-3'-trifluoromethyl) acrylophenone to give the product as crystals, m.p. 83°–84° C.

EXAMPLE 70

2-Ethyl-7-(α,α,α-trifluoro-m-tolyl)pyrazolo[1,5-a]pyrimidine-3-carbonitrile

As for Example 1, 3-amino-5-ethylpyrazole-4-carbonitrile is reacted with 3-dimethylamino-3'-(trifluoromethyl)-acrylophenone to give the product as crystals, m.p. 144°–146° C.

EXAMPLE 71

2-Ethyl-7-(m-methoxyphenyl)pyrazolo[1,5-a]pyrimidine-3-carbonitrile

As for example 1, 3-amino-5-ethylpyrazole-4-carbonitrile is reacted with 3-dimethylamino-3'-(trifluoromethyl)acrylophenone to give the product as crystals, m.p. 118°–119° C.

EXAMPLE 72

2-Ethyl-6-methyl-7-(α,α,α-trifluoro-m-tolyl)-pyrazolo[1,5-a]-pyrimidine-3-carbonitrile As for Example 1, 3-amino-5-ethylpyrazole-4-carbonitrile is reacted with 3-dimethylamino-2-methyl-3'-(trifluoromethyl) acrylophenone to give the product as crystals, m.p. 163°–164° C.

EXAMPLE 73

Methyl 2-methyl-7-(α,α,α-trifluoro-m-tolyl)pyrazolo[1,5-a]-pyrimidine-3-carboxylate As for Example 1, methyl 3-amino-5-methylpyrazole-4-carboxylate is reacted with 3-dimethylamino-3'-(trifluoromethyl)-acrylophenone to give the product as crystals, m.p. 177°–179° C.

EXAMPLE 74

Ethyl 7-(α,α,α-trifluoro-o-tolyl)pyrazolo[1,5-a]pyrimidine-3-carboxylate

As for Example 1, ethyl 3-aminopyrazole-4-carboxylate is reacted with 3-dimethylamino-2'-(trifluoromethyl)acrylophenone to give the product as crystals, m.p. 148°–149° C.

EXAMPLE 75

3-Bromo-7-(α,α,α-trifluoro-m-tolyl)pyrazolo[1,5-a]pyrimidine

To a 0.01 mole sample of 7-(α,α,α-trifluoro-m-tolyl)-pyrazolo [1,5-a]pyrimidine in 50 ml. of dichloromethane is added 0.01 mole of bromine. After standing, the mixture is worked up as for Example 15 to give the product as crystals, m.p. 138°–140° C.

EXAMPLE 76

7-(m-Fluorophenyl)pyrazolo[1,5-a]pyrimidine-3-carbonitrile

As for Example 1, 3-dimethylamino-3'-fluoroacrylophenone is reacted with 3-aminopyrazolo-4-carbonitrile in glacial acetic acid to give the product as crystals, m.p. 221.5°–223.5° C.

EXAMPLE 77

Ethyl 7-(m-tolyl)pyrazolo[1,5-a]pyrimidine-3-carboxylate

As for example 1, 3-dimethylamino-3'-methylacrylophenone is reacted with ethyl 3-aminopyrazole-4-carboxylate in glacial acetic acid to give the product as crystals, m.p. 69°–70° C.

EXAMPLE 78

2-Methoxyethyl-7-(α,α,α-trifluoro-m-tolyl)-pyrazolo[1,5-a]pyrimidine-3-carboxylate One hundred milligrams of metallic sodium is added to 50 ml. of 2-methoxyethanol and after it has dissolved, 3.35 g. of ethyl 7-(α,α,α-trifluoro-m-tolyl)pyrazolo[1,5-a]pyrimidine-3-carboxylate is added and the mixture is refluxed for one hour. On cooling, the desired compound crystallizes from the solution and is removed by filtration. Recrystallization from methylene chloride-hexane affords the product as crystals, m.p. 111°–112° C.

EXAMPLE 79

2-Dimethylaminoethyl 7-(α,α,α-trifluoro-m-tolyl)pyrazolo[1,5-a]-pyrimidine-3-carboxylate One hundred milligrams of metallic sodium is added to 25 ml. of dimethylethanolamine. After the sodium is reacted, 3.35 of ethyl 7-(α,α,α-trifluoro-m-tolyl)-pyrazolo[1,5-a]-pyrimidine is added and the mixture is refluxed for one hour. On cooling, the desired ester crystallizes from the reaction mixture and is removed by filtration. Recrystallization from methylene chloride-hexane affords the product as crystals, m.p. 119°–120° C.

EXAMPLE 80

3-(Methoxymethyl)-7-(α,α,α-trifluoro-m-tolyl)-pyrazolo[1,5-a]-pyrimidine

A suspension of 1.35 g. of 7-(α,α,α-trifluoro-m-tolyl)-pyrazolo[1,5-a]pyrimidine-3-carboxaldehyde in 90 ml. of absolute methanol is treated with 0.175 g. of sodium borohydride. After stirring for 2 hours at room temperature, excess 1 N aqueous hydrochloric acid is added and the mixture with the methanol is concentrated under reduced pressure. The solid that separates is dissolved in methylene chloride and this solution is washed with a saturated sodium bicarbonate solution and then dried (sodium sulfate). Addition of hexane to this refluxing solution causes the desired compound to crystallize, m.p. 114°–116° C.

EXAMPLE 81

3-(Ethoxymethyl)-7-(α,α,α-trifluoro-m-tolyl)-pyrazolo[1,5-a]-pyrimidine

A mixture of 2.15 g. of dimethylamine hydrochloride, 1.5 ml. of 37% formalin, and 10.5 ml. of acetic anhydride is swirled and heated gently until the reaction mixture becomes homogeneous. To the mixture is added 2.63 g. of 7-(α,α,α-trifluoro-m-tolyl) pyrazolo[1,5-a]pyrimidine and the reaction mixture is heated for 2 hours on a steam bath. The reaction mixture is evaporated to dryness and acetone is added and briefly refluxed and evaporated to dryness again. Water is added and the mixture extracted with methylene chloride. The residue, on evaporation of the solvent, when recrystallized from ethanol gave the product, m.p. 110°–111° C.

EXAMPLE 82

7-(α,α,α-Trifluoro-m-tolyl)pyrazolo[1,5-a]pyrimidine-3-carboxaldehyde

Seventy-five milliliters of dried dimethylformamide is cooled in an ice bath and 25 ml. of phosphorus oxychloride is added dropwise with swirling. To this ice cold mixture is added 19.5 g. of 7-(α,α,α-trifluoro-m-tolyl)-pyrazolo[1,5-a]pyrimidine in one portion and the reaction mixture is then heated on a steam bath for 1.5 hours. The mixture is poured onto ice and made basic (pH 10) with 10 N NaOH. The precipitated solid is removed by filtration and recrystallized from methylene chloride-hexane to give the product, m.p. 196° 198° C.

EXAMPLE 83

3-Cyano-7-(α,α,α-trifluoro-m-tolyl)pyrazolo[1,5-a]pyrimidine-2-acetonitrile

A mixture of 2.94 g. of 5-amino-4-cyano-3-cyanomethyl pyrazole and 4.86 g. of 3-dimethylamino-3'-trifluoromethylacrylophenone in 25 ml. of glacial acetic acid is refluxed for 16 hours. The reaction mixture is evaporated to dryness and then extracted with methylene chloride. This solution is washed with a saturated sodium bicarbonate solution and dried with sodium sulfate. After passage of this solution through a short column of hydrous magnesium silicate, the effluent from this column is refluxed with gradual addition of hexane until the product crystallizes. Filtration gives crystals, m.p. 180°–181° C.

EXAMPLE 84

7-Phenyl-3(α,α,α-trifluoroacetyl)pyrazolo[1,5-a]pyrimidine

A mixture of 7-phenylpyrazolo[1,5-a]pyrimidine, 50 ml. of methylene chloride and 10 ml. of trifluoroacetic anhydride is allowed to stand at room temperature overnight. Evaporation of the reaction mixture gives a residue which is redissolved in methylene chloride and washed with a saturated sodium bicarbonate solution. This dried solution, after passing through a hydrous magnesium silicate column, is evaporated and hexane added. At one point a flocculant precipitate is noted. After cooling, this material is removed by filtration. The desired product obtained in this manner is amorphorus with a softening temperature of 105°–109° C.

We claim:
1. A compound of the formula:

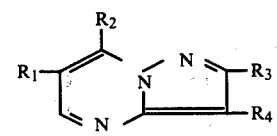

wherein $R_1$ is hydrogen or alkyl having up to 3 carbon atoms; $R_2$ is selected from the group consisting of phenyl, o-trifluoromethylphenyl, m-trifluoromethylphenyl and m-methoxyphenyl; $R_3$ is hydrogen, fluoro, chloro, bromo, cyano, cyanomethyl, carbamoyl or alkyl having up to 3 carbon atoms; and $R_4$ is selected from the group consisting of hydrogen, fluoro, chloro, bromo, formyl, carboxyl, cyano, hydroxymethyl, N-hydroxyformimidoyl, alkyl having up to 3 carbon atoms and moieties of the formulae:

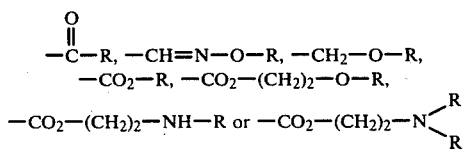

wherein R is alkyl having up to 3 carbon atoms.

2. The compound according to claim 1 wherein $R_1$ and $R_3$ are hydrogen, $R_2$ is m-trifluoromethylphenyl and $R_4$ is cyano; 7-($\alpha,\alpha,\alpha$-trifluoro-m-tolyl)-pyrazolo[1,5-a]pyrimidine-3-carbonitrile.

3. The compound according to claim 1 wherein $R_1$ and $R_3$ are hydrogen; $R_2$ is m-trifluoromethylphenyl and $R_4$ is ethoxycarbonyl; ethyl 7-($\alpha,\alpha,\alpha$-trifluoro-m-tolyl)pyrazolo[1,5-a]pyrimidine-3-carboxylate.

4. The compound according to claim 1 wherein $R_1$ and $R_3$ are hydrogen; $R_2$ is m-trifluoromethylphenyl and $R_4$ is acetyl; methyl 7-($\alpha,\alpha,\alpha$-trifluoro-m-tolyl)-pyrazolo[1,5-a]pyrimidin-3-yl ketone.

5. The compound according to claim 1 wherein $R_1$ and $R_3$ are hydrogen, $R_2$ is m-trifluoromethylphenyl and $R_4$ is N-hydroxyformimidoyl; 7-($\alpha,\alpha,\alpha$-trifluoro-m-tolyl)pyrazolo[1,5-a]-pyrimidine-3-carboxaldehyde oxime.

6. The compound according to claim 1 wherein $R_1$ and $R_3$ are hydrogen; $R_2$ is m-methoxyphenyl and $R_4$ is cyano; 7-(m-methyoxyphenyl) pyrazolo[1,5-a]pyrimidine-3-carbonitrile.

7. The compound according to claim 1 wherein $R_1$ and $R_3$ are hydrogen; $R_2$ is m-trifluoromethylphenyl and $R_4$ is methoxymethyl; 3-(methoxymethyl)-7-($\alpha,\alpha,\alpha$-trifluoro-m-tolyl)pyrazolo-[1,5-a]pyrimidine.

8. The compound according to claim 1 wherein $R_1$ and $R_3$ are hydrogen; $R_2$ is m-trifluoromethylphenyl and $R_4$ is bromo; 3-bromo-7-($\alpha,\alpha,\alpha$-trifluoro-m-tolyl)-pyrazolo[1,5-a]pyrimidine.

9. The compound according to claim 1 wherein $R_1$ is hydrogen; $R_2$ is m-trifluoromethylphenyl and $R_3$ and $R_4$ are cyano; 2-cyano-7-($\alpha,\alpha,\alpha$-trifluoro-m-tolyl)-pyrazolo[1,5-a]pyrimidine-3-carbonitrile.

10. The compound according to claim 1 wherein $R_1$ is hydrogen, $R_2$ is m-trifluoromethylphenyl, $R_3$ is cyanomethyl, and $R_4$ is cyano; 3-cyano-7-($\alpha,\alpha,\alpha$-trifluoro-m-tolyl)pyrazolo[1,5-a]-pyrimidine-2-acetonitrile.

11. The compound according to claim 1 wherein $R_1$ and $R_3$ are hydrogen, $R_2$ is m-trifluoromethylphenyl, $R_4$ is methyl; 3-methyl-7-($\alpha,\alpha,\alpha$-trifluoro-m-tolyl)-pyrazolo[1,5-a]pyrimidine.

12. Ethyl 7-(m-tolyl)pyrazolo[1,5-a]pyrimidine-3-carboxylate.

13. Ethyl 7-(3,4-xylyl)pyrazolo[1,5-a]pyrimidine-3-carboxylate.

14. Ethyl 7-(p-ethylphenyl)pyrazolo[1,5-a]pyrimidine-3-carboxylate.

15. Ethyl 7-(3,4-dimethoxyphenyl)pyrazolo[1,5-a]pyrimidine-3-carboxylate.

16. 7-(m-Fluorophenyl)pyrazolo[1,5-a]pyrimidine-3-carbonitrile.

17. 5-Phenylpyrazolo[1,5-a]pyrimidine.

18. 5-($\alpha,\alpha,\alpha$-Trifluoro-m-tolyl)pyrazolo[1,5-a]pyrimidine.

* * * * *